United States Patent [19]

Nardi

[11] Patent Number: 5,480,304
[45] Date of Patent: Jan. 2, 1996

[54] DEVICE FOR PROVIDING QUICK COUPLINGS FOR DENTAL PROSTHESES

[75] Inventor: Ezio Nardi, Casalecchio Di Reno, Italy

[73] Assignee: Rhein 83 Snc di Nardi Ezio & C., Bologna, Italy

[21] Appl. No.: 305,635

[22] Filed: Sep. 14, 1994

[30] Foreign Application Priority Data

Sep. 22, 1993 [IT] Italy .................................. BO93U0193

[51] Int. Cl.⁶ ........................ A61C 13/12; A61C 13/225; A61C 8/00
[52] U.S. Cl. ............................................ 433/172; 433/173
[58] Field of Search .................................. 433/172, 173, 433/174, 175, 176

[56] References Cited

U.S. PATENT DOCUMENTS

| | | | |
|---|---|---|---|
| 3,808,606 | 5/1974 | Tronzo | 433/173 X |
| 4,907,969 | 3/1990 | Ward | 433/173 |
| 5,071,350 | 12/1991 | Niznick | 433/173 |
| 5,073,110 | 12/1991 | Barbone | 433/173 |
| 5,092,770 | 3/1992 | Zakula | 433/172 |
| 5,194,000 | 3/1993 | Dury | 433/173 |

FOREIGN PATENT DOCUMENTS 539994 4/1955 Belgium .................................. 433/172

Primary Examiner—Nicholas D. Lucchesi
Attorney, Agent, or Firm—Guido Modiano; Albert Josif

[57] ABSTRACT

Device for providing quick couplings for dental prostheses including a substantially spherical male element which is meant to be associated with a removable part of the prosthesis and is suitable to couple to a female element which is shaped complementarily with respect to the male element and is correspondingly provided by a fixed part of the prosthesis. The male element extends from a stem which has a spherical head that is suitable to be coupled to a correspondingly spherical seat associated with the removable part of the prosthesis.

17 Claims, 4 Drawing Sheets

DEVICE FOR PROVIDING QUICK COUPLINGS FOR DENTAL PROSTHESES

BACKGROUND OF THE INVENTION

The present invention relates to a device for providing quick couplings for dental prostheses.

It is known that removable dental prostheses provided with appropriate couplings for quick anchoring to residual dental structures are currently available.

In particular, U.S. Pat. No. 5,030,094 discloses a quick coupling that ensures durable engagement and includes a spherical male element and a female element which is shaped complementarily with respect to said male element and is shaped like a sort of cap made of plastic material which is meant to be accommodated and stably retained in the removable part of the prosthesis.

Conveniently, the seat of said plastic cap is formed in a metal part which is meant to be monolithic with the removable part of the prosthesis. Said metal part is obtained preferably by lost-wax casting starting from a model, made of fettling, of the dental arch to be reconstructed.

The male element is instead supported by a pin made of metallic material which is prefabricated or obtained by casting from a calcinable plastic element. In prosthodontic couplings, said pin is threaded and is inserted and screwed in a tubular element which is meant to become monolithic with the fixed part of the prosthesis.

The male elements also act as locators for the correct assembly of the removable part of the prosthesis. However, considerable difficulties often occur during the manufacture of the prosthesis in ensuring the correct parallel arrangement of said male elements, as instead required for the optimum functionality of said prosthesis.

In order to ensure the correct parallel arrangement of the couplings, German Utility Model N. G 9309030.7 discloses a device for providing quick couplings for dental prostheses which comprises a substantially spherical male element which is meant to become monolithic with a removable part of the prosthesis and is suitable to couple with a female element which is shaped complementarily to said male element and is correspondingly provided by a fixed part of the prosthesis.

By virtue of the coupling, which allows a certain degree of rotation of the male element with respect to the female element, the pin can rotate through an angle with respect to the axis of the seat of said cap, so as to automatically find exact alignment with said cap.

However, if the couplings are not perfectly parallel the insertion of the male element in the corresponding female element can be difficult, with consequent difficulty in applying the dental prosthesis.

SUMMARY OF THE INVENTION

The aim of the present invention is to solve the above mentioned problem by providing a device that allows to provide quick couplings for dental prostheses that ensures easy insertion of the male element of said couplings in the corresponding female element even if said couplings are not perfectly parallel.

Within the scope of this aim, an object of the present invention is to provide a device for providing quick couplings for dental prostheses which is simple in concept, safely reliable in operation, and versatile in use.

This aim and this object are both achieved, according to the invention, by the present device for providing quick couplings for a dental prosthesis including a fixed part and a removable part, said device comprising: a pin element being rigidly connectable to said removable part of the prosthesis, said pin element being provided at an end thereof with a spherical seat; a stem member having a first end and a second end, said second end being constituted by a spherical head; a male element being rigidly connected to said first end of said stem member; a female element being coupleable to said fixed part of the prosthesis; wherein said male element and said female element, and respectively said spherical head and said pin element, are mutually coupleable to form spherical couplings.

BRIEF DESCRIPTION OF THE DRAWINGS

The features of the invention will become apparent from the following detailed description of a preferred embodiment of the device for providing quick couplings for dental prostheses, illustrated only by way of non-limitative example in the accompanying drawing, wherein.

DESCRIPTION OF THE PREFERRED EMBODIMENTS

Figure 4:
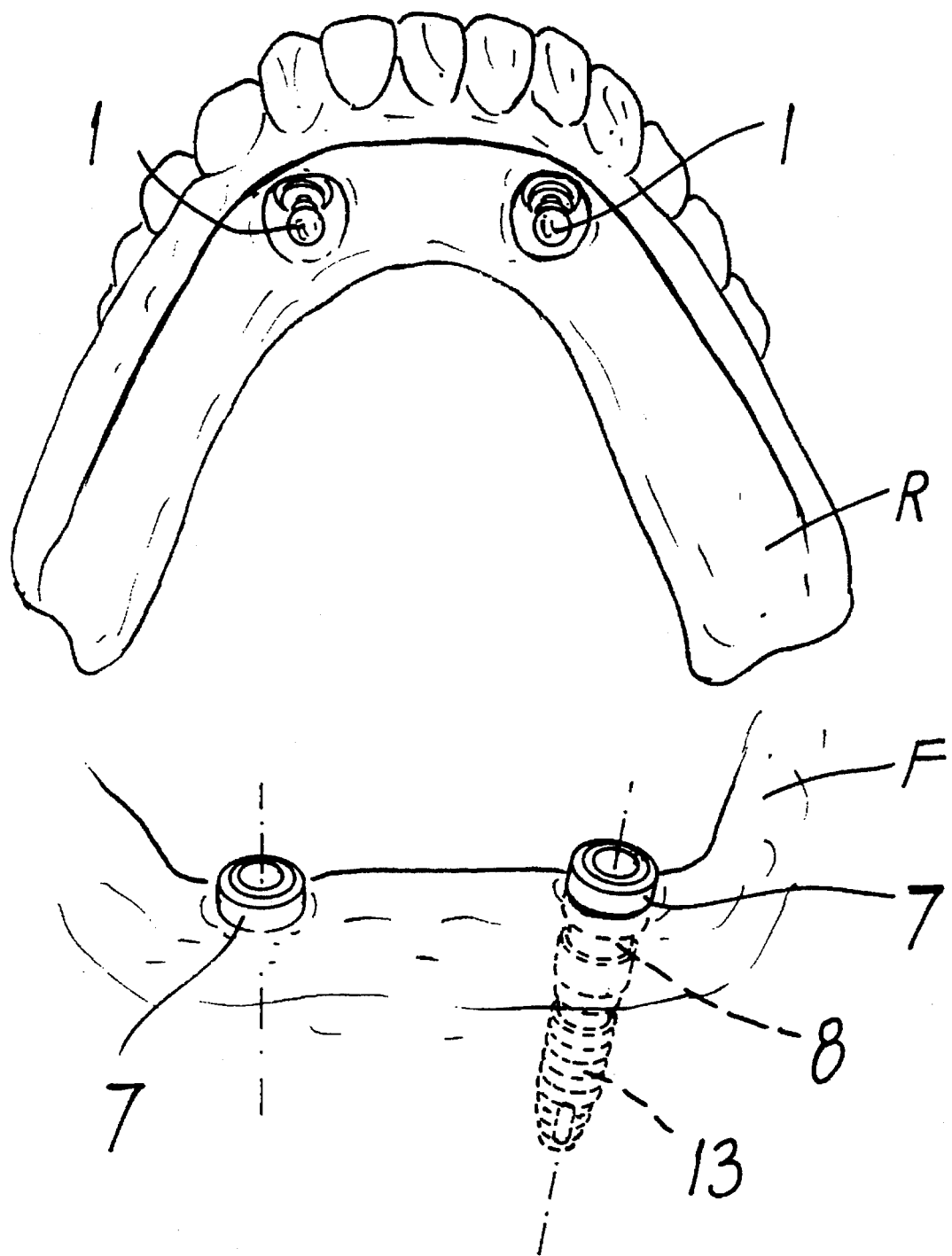
FIG. 4 is a perspective view of the fixed part and of the removable part of a prosthesis provided with the device according to the invention and shown in the ready-to-assemble configuration.

With particular reference to the above figures, the quick coupling for dental prostheses includes a substantially spherical male element 1 which extends from a first end of a stem member having at a second end thereof a spherical head 2; said spherical head 2 is suitable to be coupled to a pin element 3 which is provided particularly to be rigidly coupled to a removable part R of the prosthesis (FIG. 4). Actually, the spherical element 1 has a flattened region 2c at the base where it is joined to a cylindrical neck 2a of the stem provided with the spherical head 2; the neck 2a is connected to said spherical head by an annular recessed portion 2b.

More specifically, the spherical head 2 couples to a correspondingly spherical seat 4 formed at the end of the pin 3 and is retained inside said seat 4 by bending the border edge 3a formed by said pin 3 at the inlet of said seat 4.

Preferably, the male element 1 and the related pin 3 are made of titanium or of a high-strength sintered ceramic material.

In the illustrated case, the pin 3 has annular grooves 5 which improve the stability of the coupling to the prosthesis, generally made of resin, in which said pin is embedded. The pin 3 is in any case meant to be treated in the most appropriate manner according to the conditions in which it is used.

The male element 1 is suitable to be coupled in turn to a female element 6 which is present and has the inlet in the gum region of a fixed part F of the prosthesis (FIG. 4).

Figure 2:
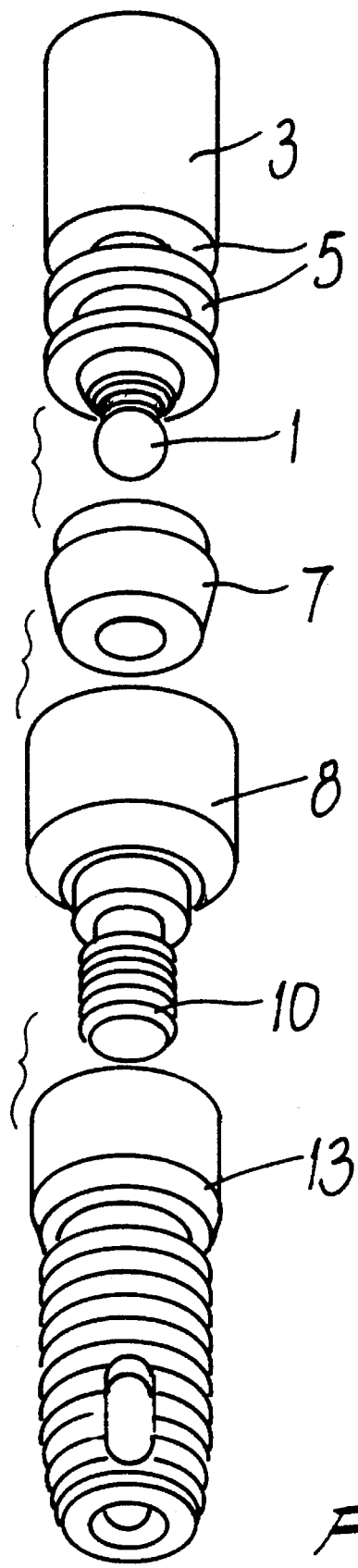
FIG. 2 is an exploded perspective view of the device according to the invention.
Figure 3:
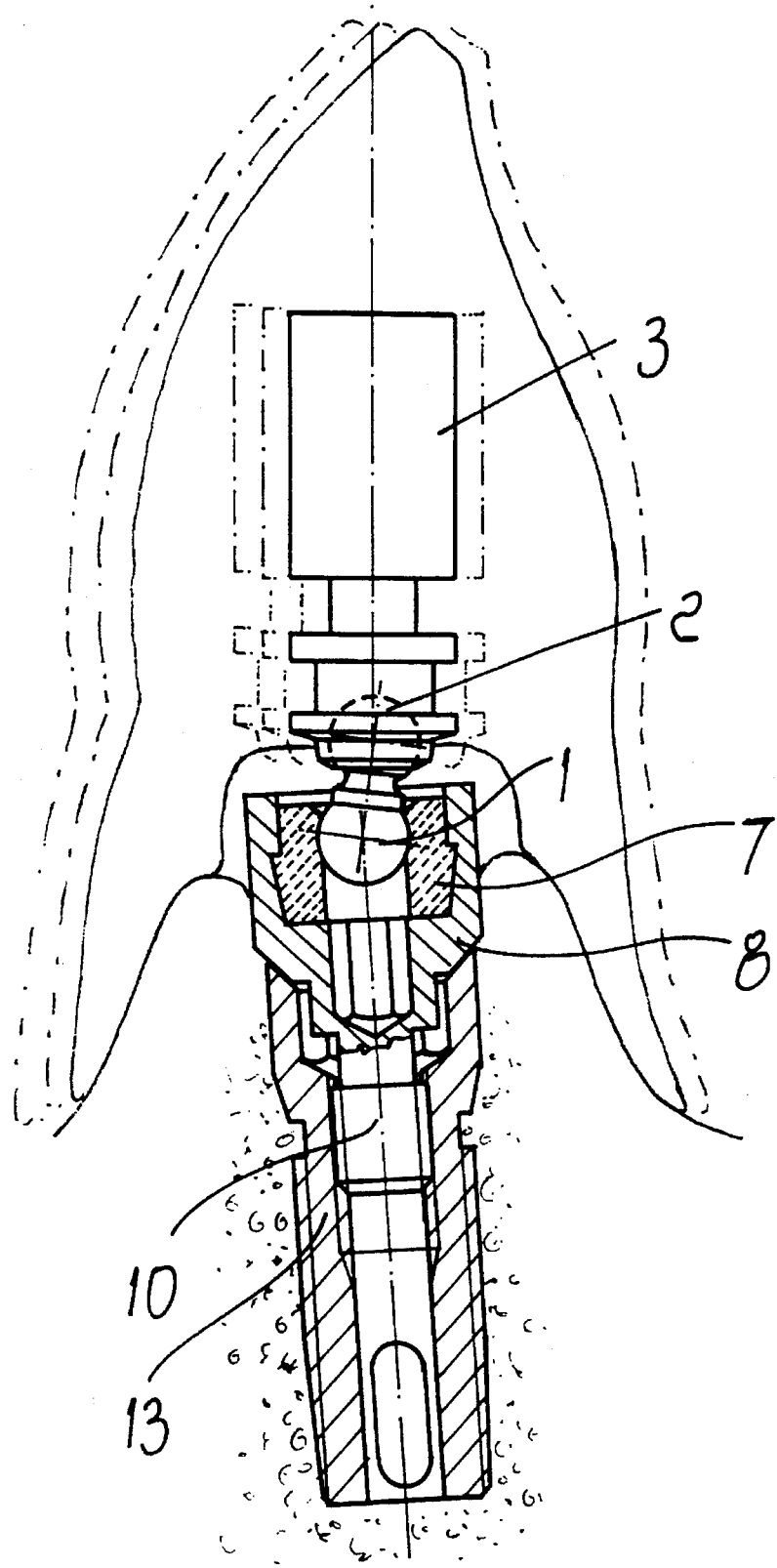
FIG. 3 is a longitudinal sectional view of the device according to the invention shown as applied to a dental prosthesis.

Said female element 6 is formed by a sort of plastic cap 7 which is meant to be accommodated and stably retained in a body 8 that is meant to be associated with a conventional tubular prosthodontic element 13 which is shown in FIGS. 2–4; said prosthodontic element 13, also known as an insert, is meant to be monolithic with the fixed part F of the prosthesis.

In practice, the cap 7 is in fact externally provided with a shoulder 7a, and the corresponding seat 9 of the body 8 is shaped complementarily to the outer surface of said cap. The cap 17 couples in a snap-together manner to said body 8 without the possibility of disengaging from said body without destroying the cap.

Preferably, the body 8 is made of titanium and is externally shaped so as to be suitable for various kinds of implant.

The body 8 extends axially so as to form a threaded cylindrical stem 10 which is meant to be screwed in said tubular insert. For screwing in the insert, the body 8 is internally provided with an axial cavity 11 that has a prism-shaped profile, for example a hexagonal one, which is meant to be engaged by an appropriate tool such as an Allen wrench. Access is allowed to the cavity 11 by means of an axial hole 12 of the cap 7.

Figure 1:
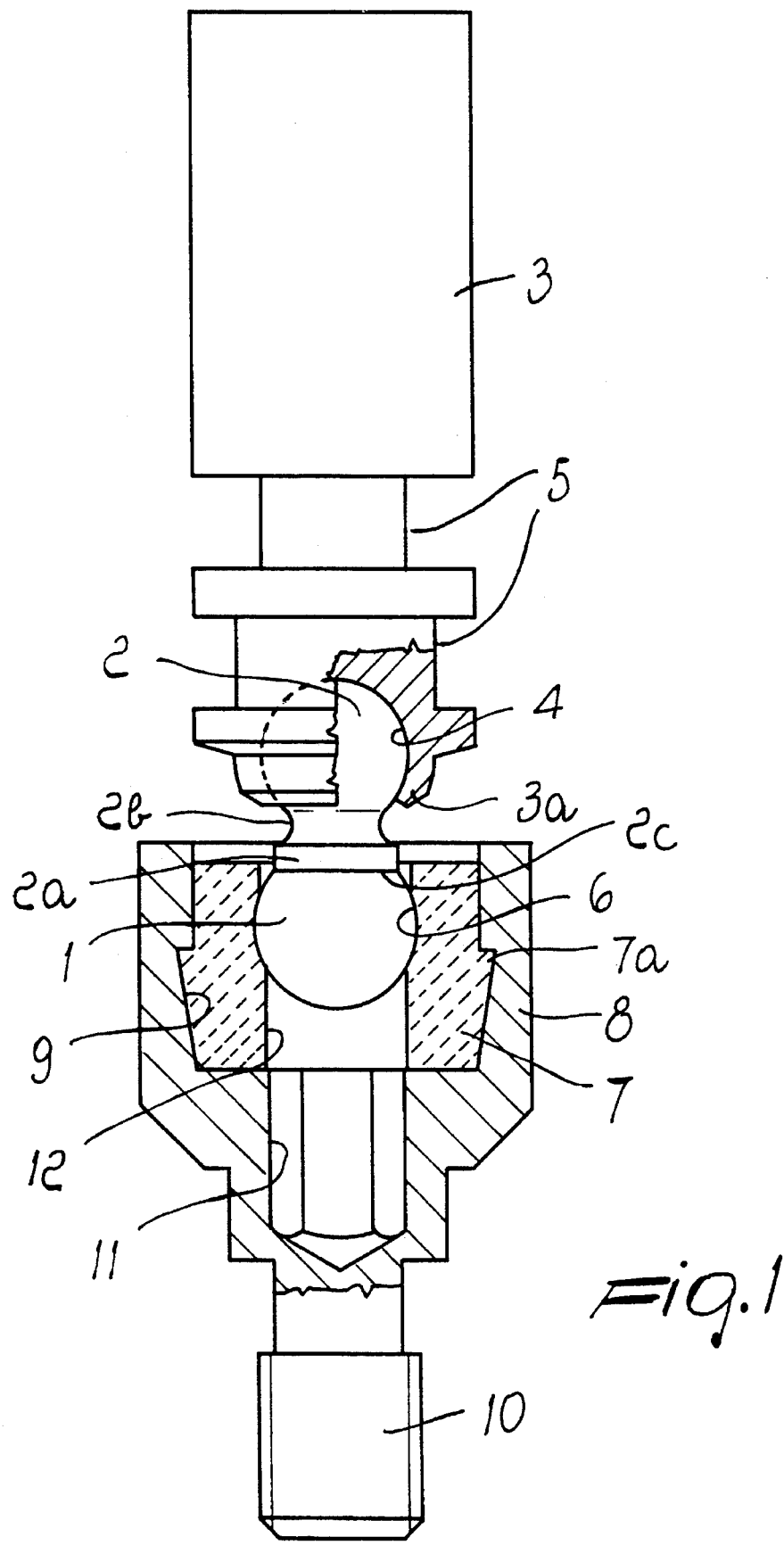
FIG. 1 is a longitudinal sectional view of the device according to the invention.

As clearly shown in FIG. 1, the through hole 12 comprises an inlet portion having a diameter which is smaller than the diameter of the male element 1, a containment portion which in fact constitutes the female element 6 and which has an inner diameter substantially equal to the diameter of the male element, and eventually an end portion.

Such end portion has a diameter smaller than the diameter of the inlet portion.

The male element 1 is adapted to be forcedly inserted through the inlet portion for being accommodated in the female element 6 which has an inner spherical surface such as to accommodate only an equatorial area of the male element.

The stem 10 is screwed fully into the insert; the body 8 passes through the gum region onto which the female element 6, meant to accommodate the male element 1, opens.

In practice, the cap 7 rigidly associated with the fixed part F of the prosthesis is affected by the spherical element 1 that protrudes from the removable part R of the prosthesis.

By virtue of the spherical coupling between the head 2 of the male element 1 and the corresponding seat 4 of the pin 3, which allows a certain degree of rotation of said male element, mating with the female element 6 is facilitated even if the coupling is not perfectly parallel. In this case the axis of the male element in fact arranges itself so as to spontaneously find the appropriate insertion configuration.

The pin 3 can furthermore rotate through an angle with respect to the axis of the body 8 as shown in FIG. 3, by virtue of the double spherical coupling provided by the male element 1, so as to find exact alignment with the cap 7. Said exact alignment is therefore obtained automatically during mating, thus ensuring the parallel arrangement of the couplings. In fact as it is clearly shown in FIG. 3 the stem member with the male element 1 assumes the appearance of a double-male element which is coupled at both ends to form the double spherical coupling which allows both the stem member and the pin 3 to perform angular movements with respect to the body 8. In this way they can assume either the position of FIG. 1, where their longitudinal axes are aligned along the same linear direction with the axis of the body 8, or any of the configurations of FIG. 3, where their axes form with the axis of the body 3 a continuous line with angularly offset portions.

To conclude, the described device allows to provide quick couplings for dental prostheses which ensure easy mutual mating of the male element and the female element of said couplings, as well as their correct parallel arrangement. In particular, it is possible to appropriately combine within the prosthesis the devices according to the invention with those disclosed in the above mentioned German Utility Model N. G 9309030.7.

The described device furthermore ensures that the engagement of the couplings between the male elements 1 and the caps 7 is safe and durable without limiting the possibility of removing the movable part of the prosthesis.

The fact should also be stressed that the coupling thus provided is advantageously very close to the gum region.

Last but not least, the prior art coupling devices are conceived so as to provide a fixed, rigid coupling between the two fixed and removable parts of the prosthesis, for it is generally believed that a coupling allowing slight relative movements between such two parts might cause the patient to feel discomfort during chewing.

Contrary to such widespread belief, it has now been practically ascertained that slight relative movements, as allowed by the device according to the present invention, have a surprisingly benefic effect on the health of the patient's gums and dental roots.

It has been in fact ascertained that shaky dental roots bearing coupling devices according to the invention tend to rapidly consolidate. Furthermore, a highly efficient massaging action of the removable part of the prosthesis on the patient's gum appears to occur, with a strong, benefic effect for the user.

Due to the particular configuration of the plastics cap through hole 12, the male element 1 is elastically supported inside the female element 6. The coupling according to the present invention is therefore highly efficient for absorbing the shocks due to even energetic chewing.

In the practical embodiment of the invention, the materials employed, as well as the shape and the dimensions, may be any according to the requirements.

What is claimed is:

1. Device for providing quick couplings for a dental prosthesis including a fixed part and a removable part, said device comprising:

a pin element being rigidly connectable to said removable part of the prosthesis, said pin element being provided at an end thereof with a spherical seat and defining a first longitudinal axis;

a stem member having a first end and a second end, said second end being constituted by a spherical head, said spherical head being rotatably accommodated in said spherical seat for forming a spherical coupling;

a male element being rigidly connected to said first end of said stem member, said stem member and said male element defining a second longitudinal axis thereof;

a female element being accommodated in a body, said body being coupleable to said fixed part of the prosthesis, said female element accommodated in said body defining a third longitudinal axis, and said male element being rotatably accommodated in said female element for forming a further spherical coupling, said stem member and said pin element being angularly movable with respect to said body between a position in which said first, second and third longitudinal axes are aligned along a same linear direction and a position in which said first, second and third longitudinal axes form a continuous line with angularly offset portions.

2. Device according to claim 1, wherein said male element has an outer diameter corresponding to an inner diameter of said female element, said female element comprising an inner spherical surface for accommodating only an equatorial region of said male element.

3. Device according to claim 1, wherein said spherical head is adapted to be retained inside said seat formed in said pin by folding a border edge of said seat.

4. Device according to claim 1, wherein said male element has a flattened region, said flattened region being joined to a cylindrical neck of said stem, said neck being connected to said spherical head by an annular groove.

5. Device according to claim 1, wherein said female element is formed by a cap made of plastic material, the outer surface of said cap being shaped complementarily with respect to a corresponding seat formed in said body, the body being screwable in a tubular prosthodontic element, said prosthodontic element being adapted to become monolithic with said fixed part of the prosthesis.

6. Device according to claim 5, wherein said cap has an axial through hole, said hole comprising: an inlet portion having a diameter which is smaller than the diameter of said male element; a containment portion constituting said female element; and an end portion having a diameter smaller than the diameter of said inlet portion, whereby said male element is forcedly insertable through said inlet portion for being accommodated in said female element at said equatorial region thereof.

7. Device for providing quick couplings for a dental prosthesis including a fixed part and a removable part, said device comprising:

a pin element being rigidly connectable to said removable part of the prosthesis, said pin element being provided at an end thereof with a spherical seat;

a stem member having a first end and a second end, said second end being constituted by a spherical head, said spherical head being rotatably accommodated in said spherical seat for forming a spherical coupling;

a male element being rigidly connected to said first end of said stem member;

a female element being coupleable to said fixed part of the prosthesis, said female element being enclosed in a cap, said cap having an axial through hole, said hole having an inlet portion with a diameter which is smaller than the diameter of said male element, a containment portion defining said female element, and an end portion having a diameter smaller than the diameter of said inlet portion, whereby said male element is forcedly insertable through said inlet portion for being rotatably accommodated in said female element to form a further spherical coupling.

8. Device according to claim 7, wherein said male element has an outer diameter corresponding to an inner diameter of said female element, said female element comprising an inner spherical surface for accommodating only an equatorial region of said male element.

9. Device according to claim 7, wherein said spherical head is adapted to be retained inside said seat formed in said pin by folding a border edge of said seat.

10. Device according to claim 7, wherein said male element has a flattened region, said flattened region being joined to a cylindrical neck of said stem, said neck being connected to said spherical head by an annular groove.

11. Device according to claim 7, wherein said cap is made of plastic material, the outer surface of said cap being shaped complementarily with respect to a corresponding seat formed in a body, said body being screwable in a tubular prosthodontic element, said prosthodontic element being adapted to become monolithic with said fixed part of the prosthesis.

12. Device for providing quick couplings for a dental prosthesis including a fixed part and a removable part, said device comprising:

a pin element being rigidly connectable to said removable part of the prosthesis, said pin element being provided at an end thereof with a spherical seat;

a stem member having a first end and a second end, said second end being constituted by a spherical head, said spherical head being rotatably accommodated in said spherical seat for forming a spherical coupling;

a male element being rigidly connected to said first end of said stem member, whereby said stem member and said male element defining a double-male element;

a female element being accommodated in a body, said body being coupleable to said fixed part of the prosthesis so that an inlet of said female element opens at a patient's gum region, and said male element being rotatably accommodated in said female element for forming a further spherical coupling.

13. Device according to claim 12, wherein said male element has an outer diameter corresponding to an inner diameter of said female element, said female element comprising an inner spherical surface for accommodating only an equatorial region of said male element.

14. Device according to claim 12, wherein said spherical head is adapted to be retained inside said seat formed in said pin by folding a border edge of said seat.

15. Device according to claim 12, wherein said male element has a flattened region, said flattened region being joined to a cylindrical neck of said stem, said neck being connected to said spherical head by an annular groove.

16. Device according to claim 12, wherein said female element is formed by a cap made of plastic material, the outer surface of said cap being shaped complementarily with respect to a corresponding seat formed in said body, the body being screwable in a tubular prosthodontic element, said prosthodontic element being adapted to become monolithic with said fixed part of the prosthesis.

17. Device according to claim 16, wherein said cap has an axial through bole, said hole comprising: an inlet portion having a diameter which is smaller than the diameter of said male element; a containment portion constituting said female element; and an end portion having a diameter smaller than the diameter of said inlet portion, whereby said male element is forcedly insertable through said inlet portion for being accommodated in said female element at said equatorial region thereof.

* * * * *